United States Patent
Cheng et al.

(10) Patent No.: US 6,234,174 B1
(45) Date of Patent: May 22, 2001

(54) URETHRAL COMPRESSION DEVICE

(75) Inventors: Gordon Cheng, Carlisle; Sanjaya Kumar, Southborough, both of MA (US)

(73) Assignee: UroScientific, Incorporated, Woburn, MA (US)

( * ) Notice: Subject to any disclaimer, the term of this patent is extended or adjusted under 35 U.S.C. 154(b) by 0 days.

(21) Appl. No.: 09/067,522

(22) Filed: Apr. 28, 1998

(51) Int. Cl.[7] .................................................. A61F 5/48
(52) U.S. Cl. .............................................. 128/885; 600/29
(58) Field of Search ...................... 128/846, 885, 128/886, DIG. 25; 600/29–31

(56) References Cited

U.S. PATENT DOCUMENTS

| | | | |
|---|---|---|---|
| 2,564,399 | 8/1951 | Franken ................... | 128/283 |
| 3,147,754 | * 9/1964 | Koessler .................. | 128/885 |
| 3,812,841 | 5/1974 | Isaacson ................... | 128/1 R |
| 3,866,611 | 2/1975 | Baumrucker .............. | 128/346 |
| 4,139,007 | * 2/1979 | Diamond .................. | 128/885 |
| 4,534,353 | 8/1985 | de Leur et al. ........... | 128/346 |
| 4,555,242 | 11/1985 | Saudagar .................. | 604/96 |
| 4,800,900 | 1/1989 | French ..................... | 128/885 |
| 4,804,375 | 2/1989 | Robertson ................. | 604/323 |
| 4,880,016 | 11/1989 | Warth et al. .............. | 128/885 |
| 4,942,886 | * 7/1990 | Timmons .................. | 128/885 |
| 5,014,757 | 5/1991 | Donaldson et al. ........ | 141/114 |
| 5,184,629 | 2/1993 | Erickson et al. .......... | 128/885 |
| 5,211,640 | 5/1993 | Wendler ................... | 604/349 |
| 5,263,947 | 11/1993 | Kay ......................... | 604/331 |
| 5,415,179 | 5/1995 | Mendoza .................. | 128/842 |
| 5,439,007 | * 8/1995 | Fischer .................... | 128/885 |
| 5,569,297 | 10/1996 | Makower et al. ......... | 606/201 |
| 5,571,125 | 11/1996 | Chadwick ................. | 606/157 |
| 5,671,755 | 9/1997 | Simon et al. ............. | 128/885 |

FOREIGN PATENT DOCUMENTS

| | | |
|---|---|---|
| 1616477 | 7/1967 | (DE) . |
| 41 35 502 | 10/1991 | (DE) . |
| 41 35 502 C1 | 2/1993 | (DE) . |
| 0 292 162 A1 | 11/1988 | (EP) . |
| 0 407 218 A1 | 7/1990 | (EP) . |
| 0 407 218 A1 | 1/1991 | (EP) . |
| 0 850 603 A1 | 7/1998 | (EP) . |
| WO 90/11063 | 10/1990 | (WO) . |
| WO 98/14146 | 4/1998 | (WO) . |
| 98/22039 | 5/1998 | (WO) . |

* cited by examiner

*Primary Examiner*—Michael A. Brown
(74) *Attorney, Agent, or Firm*—Hamilton, Brook, Smith & Reynolds, P.C.

(57) ABSTRACT

A urethral compression device prevents male urinary incontinence by compressing the urethra with a continuous, C-shaped structure which includes a curvilinear compression element extending from the inside surface of the structure. The urethral compression device compress the urethra without applying undue force to other parts of the penis. The device incorporates a ratchet mechanism on the ends of the C-shaped structure for the purpose of securing the device in a locked position. The device is designed to allow the user to manipulate the device using only one hand, if so desired.

18 Claims, 4 Drawing Sheets

URETHRAL COMPRESSION DEVICE

BACKGROUND OF THE INVENTION

Male urinary incontinence can result from a variety of physical or neurological conditions. The incidence of incontinence increases with advanced age. Surgical treatment of prostate cancer or benign prostatic hyperplasia (BPH), such as radical prostatectomies, open or transurethral prostatectomy, and trauma to the membranous urethra or bladder neck can all cause temporary or permanent incontinence in men.

Existing external compressive incontinence control devices are based on the principle that if the entire cross-section of the penile shaft is sufficiently compressed, the urethra will be correspondingly flattened to prevent any urine leakage. In order to prevent the urine leakage, the penis must be flattened to about 40% or more of the normal penile diameter. When a conventional penile clamp is used with this level of compression, the major side effect is constriction of blood vessels and prevention of blood circulation to the penis. While most users of the penile clamps of these types learn to periodically remove the clamps to temporarily restore blood circulation, it is nonetheless a major inconvenience. In addition, these conventional devices are heavy and bulky, uncomfortable and insufficiently discreet.

Others have recognized that it would be desirable to selectively compress the urethra, which is situated along the central underside of the penile shaft, without exerting undue compression of the entire penile shaft. While these devices compress the urethra more than the body of penis, the devices are either too bulky, which detracts from the user's comfort level and privacy, or are comprised of many components which increase the complexity and cost of the device and the probability of failure. Also, many of the devices require two hands for application or removal.

SUMMARY OF THE INVENTION

The urethral compression device has an arced shaped element having a first and a second arm. A compression element that applies pressure is carried by the arced element for compressing the urethra. The compression device can be made of a molded plastic material that is positioned in an open state when in an unstressed condition. The user bends one arm to connect the ends of the arms together and places the device under stress in the closed position. In a preferred embodiment, the user can easily remove the device when the arc shaped element is in the open unstressed state.

In a preferred embodiment of the invention, the pressure applying or compression device has a width of between 100 percent and 150 percent of the diameter of the urethra for optimally compressing the urethra and minimally compressing the rest of the penis. The device can be fabricated in a number of different sizes as needed.

In a preferred embodiment, the device has a latching mechanism including a plurality of teeth carried by one arm and a pawl on the other arm to engage the teeth for retaining the arced shaped element in a closed position. The arced shaped element is biased towards an open position such that release of the arms opens the device.

The urethral compression device provides a male urinary incontinence control device that is effective, non-invasive, reliable, comfortable and easily adjustable without complicated construction, adjustment procedures, or accessories. In addition, the design of the device also ensures that the user is able to maintain a high degree of privacy without being noticed by others when the user is wearing and manipulating the device.

By applying pressure selectively to the area of urethra, the urethra can be sufficiently compressed or occluded to prevent urine flow without exerting undue pressure to other parts of the penis or reducing blood circulation.

The urethral compression device is structured without an apparent localized hinge point which eliminates a structural weak link in the device. Because of the properties inherent in the construction materials, the device is provided with sufficient flexibility to allow the opening and closing of the pair of ends.

The urethral compression device can be opened for urination, closed after urination, and adjusted to the desired degree of compression by the user using only one hand, without the need for necessarily using the other hand.

The urethral compression device does not need to be removed from the penis in order to allow the user to urinate. When the device is in place and is opened for urination, the ends of the device springs open such that the opened device remains on the penis shaft. This functionality is provided to avoid the necessity of removing the device from the penis shaft, when it is supported by the user during urination.

The size, weight and operational simplicity afford a particular discreteness to this invention. The design of the invention allows the wearer to use the urethral compression device without detection since the invention does not inhibit normal body movements. Because of the release mechanism, the invention fits around the penile shaft without noticeable levers or switches necessary to unclasp the device. The small size of the invention does not add obvious volume bulk beneath user's clothing.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 2:
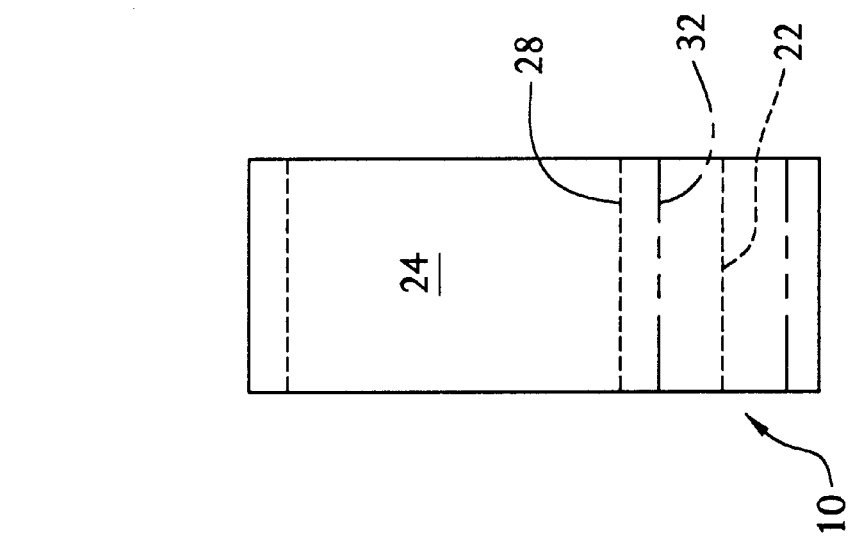
FIG. 2 is a side view of the urethral compression device.

Referring to the drawings in detail, where like numerals indicate like elements, there is illustrated an urethral compression device in accordance with the present invention designated generally as 10.

The urethral compression device 10 is generally an arced shaped structure 12 having an upper arm 14 and a lower arm 16. In this embodiment, the arced structure 12 has generally a "C" shaped structure. Each of the arms 14 and 16 terminate in a first end 18 and a second end 20 where the ends extend around an arc of at least 270 degrees. The arms 14 and 16 are adapted to couple as explained below to form a generally cylindrical compression device 10.

Figure 1:
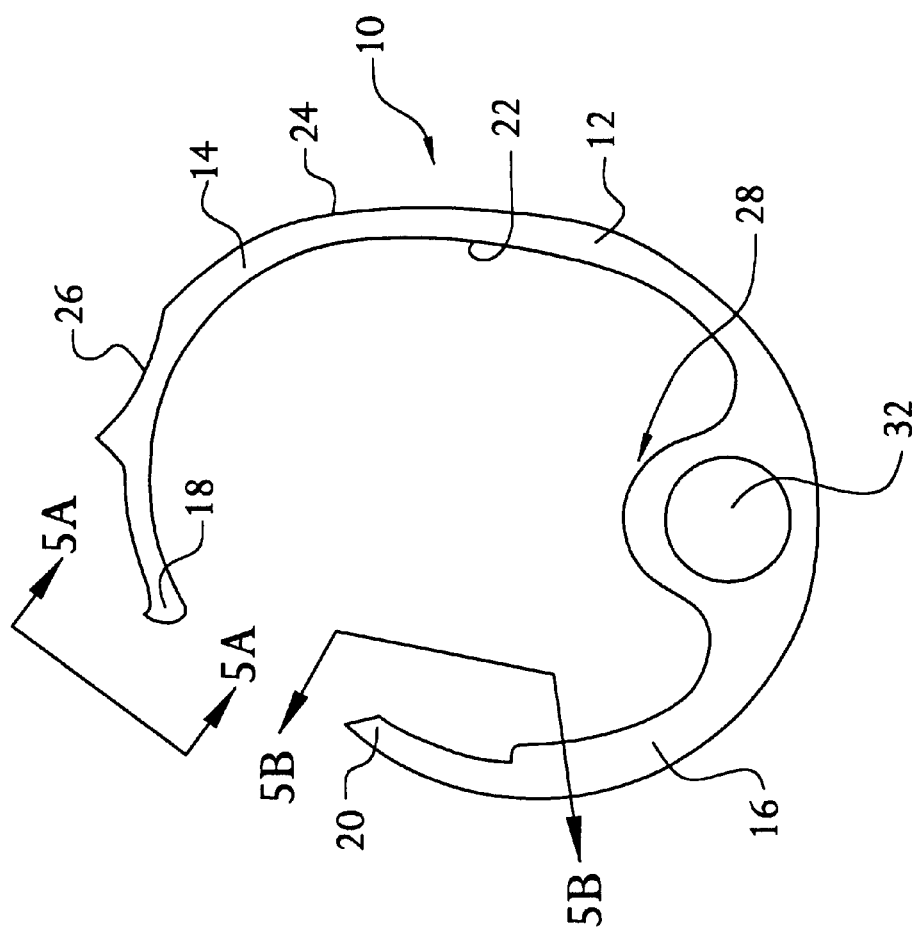
FIG. 1 is a front view of a urethral compression device according to this invention in an open position.

In a preferred embodiment, the structure 12 is manufactured as one continuous piece of material. The material is formed such that the structure 12 is biased to an open position shown in FIG. 1, wherein the first end 18 and the second end 20 are spaced from each other, and not engaged. The structure 12 in the open position receives the penis without compressing the penis as described below.

The device 10 has an inner surface 22 and an outer surface 24. The device 10 can have a thumb tab 26 on the outer surface 24 of the upper arm 14. The device 10 has a pressure applying element 28 projecting inwardly on the inner surface of the lower arm. The pressure applying element 28 has a raised portion which is sufficiently wide to optimally compress the urethra to prevent urine leakage while minimally compressing the bulk of the penis.

In a preferred embodiment, the pressure applying element 28 extends radially inward and is formed integrally as one piece with the arced shaped structure 12. The radially extending element 28 may be formed with a hole 32, or a cavity, with various shapes or geometries for minimizing the weight of the device 10. The presence or absence of a hole does not change the mode of operation.

In a preferred embodiment, the urethral compression device 10 is molded or extruded and made of a polymer material. The thickness of the arms 14 and 18 of the arced shaped structure 12 is generally in a range of 1 mm to 5 mm, and between 1 mm to 2 mm in a preferred embodiment. The device can be fabricated with a variety of polymer materials such as polyethylene, polypropylene, nylon, or polycarbonate, either in pure form, plasticized form, or composited with other polymers or filler materials. The filler material can include carbon fiber, glass fiber or other suitable filler. The device can also be constructed with an inner core of one material, such as a metal, and outer surface of some other material such as a polymer by coating, lamination or other adhesion techniques.

In a preferred embodiment, the element 28 is cylindrically shaped and has a diameter in the range of 10–15 mm. In order to achieve the desired benefits of this invention, both the size of the arced structure 12 and the element 28 are tailor to fit to the individual users. This is accomplished by presenting the urethral compression devices in a series of sizes in which arced shaped structure 12 will vary by the size of the penis and the element 28 will vary in accordance with the size of the urethra, as explained below.

A side view of the urethral compression device 10 is shown in FIG. 2. The device 10 is generally uniform in its width. The inner surface of the upper arm 22 is shown in hidden line. The inner surface of the lower arm including the pressure applying element 28 is shown in hidden line. The hole 32 extending through the element 28 is shown in phantom. In a preferred embodiment, the urethral compression device 10 has a width in the range of 10 mm to 25 mm and in the most common size having an approximate width of 15 mm.

Figure 3:
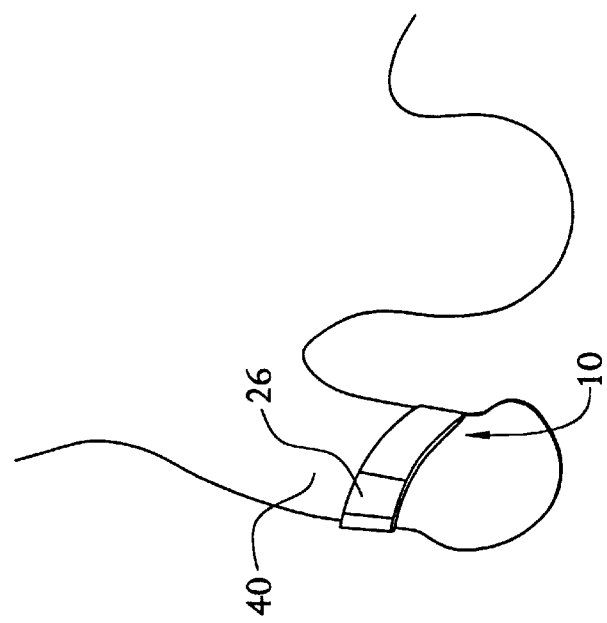
FIG. 3 is a perspective view of the urethral compression device in a closed position encircling the penis.

FIG. 3 illustrates the urethral compression device 10 on a penile shaft 40. The user typically slides the urethral compression device 10 over the penis 40, however, the arms 14 and 16 can be sufficiently separate such that the penis can pass between the upper end 18 and the lower end 20 shown in FIG. 1.

Figure 4:
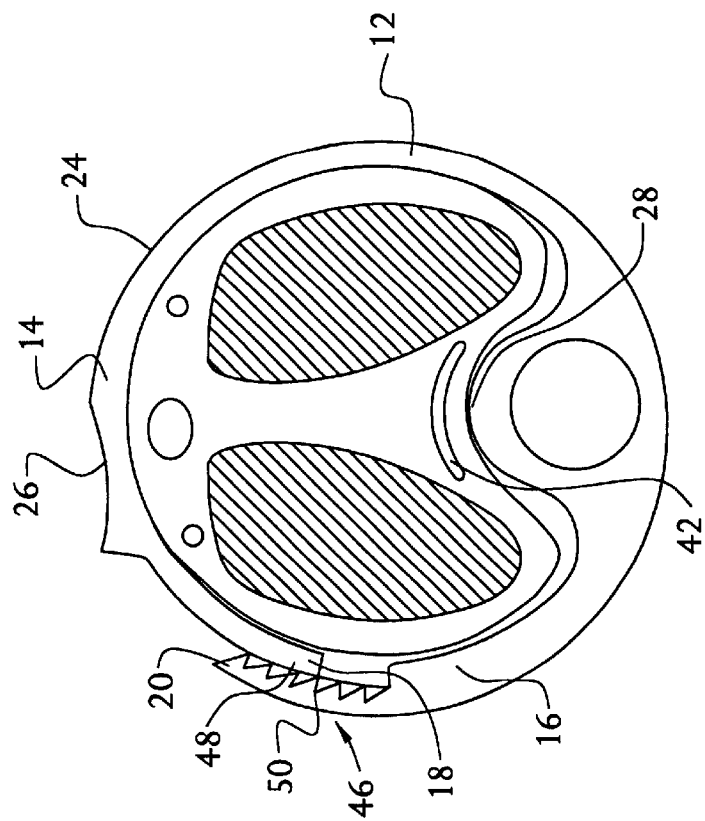
FIG. 4 is a cross sectional view of the urethral compression device in a closed position encircling the penis.

With the urethral compression device 10, in an open position, encircling the penis 40, the user positions the device 10 such that the pressure applying element 28 is located under the urethra 42, as seen in FIG. 4. The user presses the thumb tab 26, while holding the lower arm 16 of the urethral compression device 10 with other fingers.

Still referring to FIG. 4, the arms 14 and 16 of the arced structure 12 have a latching mechanism 46 near the ends 18 and 20 to hold the urethral compression device 10 in a closed position, as shown. In a preferred embodiment, the latching mechanism 46 has a pawl 48 on one arm and a plurality of ratchet teeth 50 on the other arm.

Figure 5B:
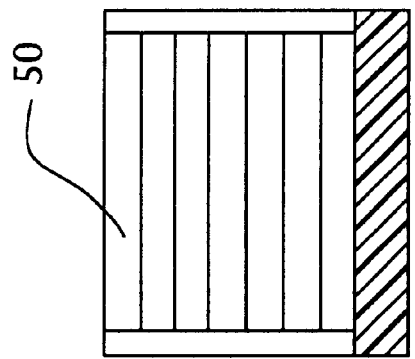
FIG. 5B is a sectional view of the ratchet teeth taken along line 5B—5B in FIG. 1.
Figure 5A:
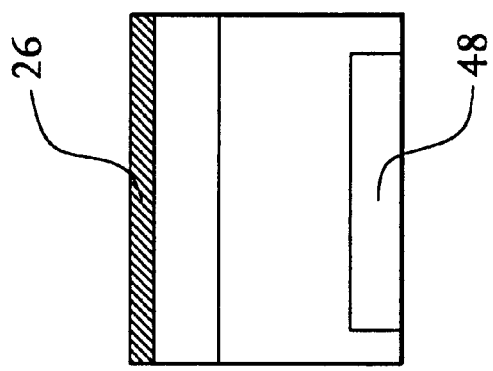
FIG. 5A is a sectional view of the pawl taken along line 5A—5A in FIG. 1.

One of the arms, the upper arm 14 as shown in FIG. 4, has the pawl 48 projecting outward. The pawl 48 extends across over half of the width of the device 10 as seen in FIG. 5A.

The other arm, the lower arm 16 as shown in FIG. 4, has the plurality of ratchet teeth 50 projecting inward. The teeth 50, similar to the pawl 48, extend across over half the width of the device as seen in FIG. 5B.

In the preferred embodiment, the ratchet teeth 50 are formed on the lower arm 16 and the pawl 48 is formed on the upper arm 14. It is recognized that the arrangement can be reversed with the pawl on the lower arm and the ratchet teeth on the upper arm. It is further recognized that the arrangement in which the ratchet teeth are made to project outward with a corresponding inward projecting pawl is also within the context of this invention.

Referring back to FIG. 4, the ends 18 and 20 of the arms 14 and 16 are ramped so that upon sliding the arms together, the pawl 48 moves into engagement with one of the ratchet teeth 50. The interlocking of the two ends 18 and 20 is designed to provide audible "clicks" when the pawl 48 snaps into each locking position with the teeth 50. The sound serves to notify the user how many ratchet teeth 50 the pawl 48 has passed or engaged so that user can determine when the precise engagement position of the device is reached. In the preferred embodiment of the invention, the user must exert 1.5–3.0 pounds force on the arms 14 and 16 to cause the two ends 18 and 20 to initially engage.

The thumb tab 26, in addition to being used to direct the proper force for engaging the pawl 48 with the ratchet teeth 50, can also be used for unclasping device. Once in place, the user can unclasp the device either by depressing the thumb tab 26 toward penis 40 or by prying away the inclined tip of the lower arm 16 by approximately 1 mm with a tip of a finger to disengage the pawl 48 from the ratchet teeth 50, while holding the base of the device in the palm of the hand. Either of these procedures can be performed using only one hand. The inherent elasticity of the material and the design of the structure itself permits the device to spring to the open position when the pawl 48 is disengaged from the ratchet teeth 50.

In alternate embodiments, other methods can be used to cause the device to spring to the open position. One such method includes varying the width of the urethral compression device 10 along its circumference in specific areas. Decreasing the width of the urethral compression device 10 will increase the flexibility of the material in that area.

Another method includes varying the thickness of the urethral compression device 10 in certain areas. Decreasing the thickness of the urethral compression device 10 in one area will increase the flexibility of the compression device 10 in that area.

Another method to tailor the amount of force needed to open and close the urethral compression device 10 is by choosing a material with a specific modulus of elasticity.

The modulus of elasticity of the urethral compression device 10 will control the extent to which the device springs to an open position when unclasped. A device 10 comprised of a material with a high modulus of elasticity will spring open faster than a device 10 comprised of a material with a lower modulus.

Adding bracing or ribbing to certain areas of the outer circumference of the device 10 also controls the flexibility of the device 10, allowing the device 10 to spring to an open position in certain cases. The addition of bracing or ribbing would decrease the flexibility of the device 10 in general. An area of the urethral compression device 10 with no bracing has a greater degree of flexibility than an area with bracing. It is recognized that any or all of these tailoring methods can be used alone or in combination with each other to produce the desired flexibility of the device 10.

The pressure applying device 28 of the urethral compression device 10 has a width that compresses the user's urethra 42 while preventing the user from feeling pinched by unnecessary compression of the penile shaft 40. When the device is in the open position and has been correctly fitted for the user's anatomy, it will accommodate the penis in an uncompressed state. When the device is in a closed position, the pressure applying element 28 provides a pre-determined degree of depression necessary for preventing involuntary urinary flow.

The ratchet teeth 50 and the pawl 48 of the latching mechanism 46 allow for the graduated adjustments in the degree of compression of the user's urethra 42.

To further understand how the urethral compression device 10 works, a brief description of the male urinary tract is needed. The inner diameter of the urethra, which varies among individuals, could range from 18 to 30 French (or 6 millimeter to 9.5 millimeter) (3 French =1 mm). The wall thickness of urethra varies between 1 to 1.5 mm. The outer diameter of the urethra varies from 7 to 11.5 mm.

In order to completely prevent the leakage of the urine with a penile clamping device, the vertical dimension of the urethra needs to be compressed into no more than the two wall thickness of the urethra. For example, let us use some typical measurements:

Penile outer diameter—31.8 mm
Urethra inner diameter—8.3 mm
Urethra outer diameter—10.7 mm
Urethra wall thickness—1.2 mm With the above typical measurements, the urethra vertical dimension (or the urethra outer diameter) must be flattened by compression from 10.7 mm to no more than 2.4 mm (two urethra wall-thickness). This represents a "degree of compression," defined as reduction in the outer urethra vertical dimension in the compressed state from the uncompressed urethra outer diameter (10.73−[2×1.2]=8.33) divided by the uncompressed urethra outer diameter, (10.7), expressed in percentage, of 78%. (0% represents no compression and 100% represent total compression.)

The urethral compression device 10 has the pressure applying element 28 at the base of the device 10 to flatten the urethra. The size of this element 28 is approximated by the outer diameter of the urethra. If the penile OD=31.8 mm (same as the in the above illustration) and the element 28 OD is assumed to be 13.914 mm (30% larger in diameter than the urethra OD of 10.7 mm), the overall resultant degree of compression for this device can be computed to be 19% by taking the ratio of the cross-sectional area of the penis compressed by the element 28, or simply the pressure applying element area, and the cross-sectional area of the un-compressed penis. A higher degree of compression corresponds to a stronger feeling of being pinched. For comparison, to effect the same degree of urethra flattening, the conventional penile clamping devices require a degree of depression of 78%.

In a preferred embodiment, the urethral compression device 10 is sized for the user such that the inner diameter of the circle formed by the closed device with the pressure applying element 28 removed is the same diameter as the outer diameter of the penis. The urethral compression device 10 in the open position receives the penis without the pressure applying element 28 compressing the urethra. The pressure applying element 28 has a size in the range of 100% to 150% of the outer diameter of the urethra. In a preferred embodiment, the element 28 is in a range of 110% to 140% of the diameter of the urethra.

Figure 6:
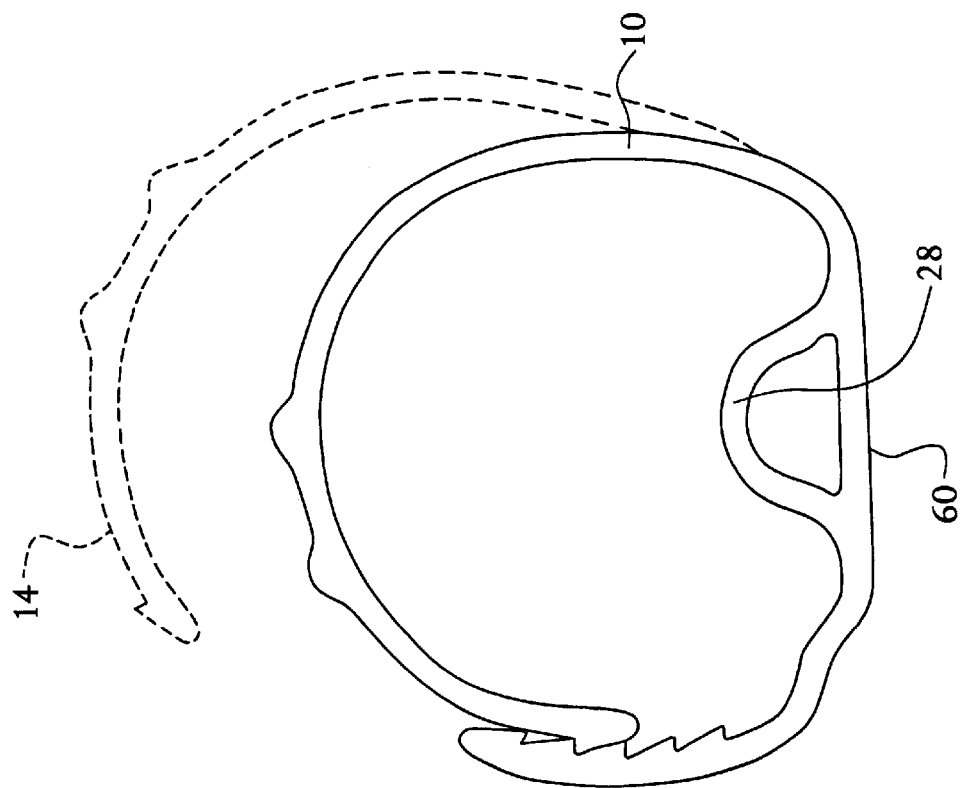
FIG. 6 is a front view of an alternate embodiment of a urethral compression device in a closed position. The upper arm in an open position is shown in phantom.

FIG. 6 shows a preferred embodiment of the invention in a closed position. The invention has a flat surface 60 which is located distal to the pressure applying element 28. The flat surface 60 provides the user some frame of reference when applying the invention to a penis wherein the flat surface 60 can be used by the user to locate the urethra. When installed properly, the flat surface 60 will be the lower surface. This will cause the element 28 to align with the wearer's urethra, thus allowing proper installation of the device.

The upper arm 14 is shown in phantom in FIG. 6. The penis fits in an uncompressed state into the urethral compression device 10 when the urethral compression device 10 is in the open position.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A urethral compression device comprising:
   an arc shaped member having a first end and a second end such that the ends move from a closed position extending around the urethra to an open position in response to an intrinsic stress in the member;
   a compression element carried by the arc shaped member that compresses the urethra, the compression element including a pressure applying element, a cavity, and a distal surface extending about the cavity; and
   a connector that connects the first end and the second end in the closed position such that the arc shaped member is under stress.

2. The urethral compression device of claim 1 wherein the arc shaped member has a "C" shape in the open position.

3. The urethral compression device of claim 2 wherein the connector further comprises a latching mechanism carried by the ends that retains the "C" shaped member in a closed position.

4. The urethral compression device of claim 3 wherein the latching mechanism has a plurality of teeth on one end of the "C" shaped element and a pawl on the other end of the "C" shaped element.

5. The urethral compression device of claim 1 wherein the compression element extends radially inward from the arc shaped member.

6. The urethral compression device of claim 5 wherein the compression element is generally cylindrical and between 10 mm and 15 mm in diameter.

7. The urethral compression device of claim 6 wherein the compression element is between approximately 13 mm and 14 mm in diameter.

8. The urethral compression device of claim 1 further comprising a thumb tab formed on the outer surface of the "C" shaped element that receives a thumb of the user.

9. A urethral compression device comprising:
- a "C" shaped element having an inner surface and an outer surface, the "C" shaped element having a first arm and a second arm;
- the first arm of the "C" shaped element having a pawl and the second arm of the "C" shaped element having a plurality of teeth such that the pawl engages at least one of the teeth to retain the "C" shaped element in a closed position;
- a thumb tab formed on the outer surface of the "C" shaped element that receives a thumb of a user to move the "C" shaped element between an open position and the closed position; and
- a compression element formed integrally with the "C" shaped element and extending inwardly for compressing the urethra, the compression element having a width of between 100 percent and 150 percent of the urethra.

10. The urethral compression device of claim 9 wherein the curvilinear element is generally cylindrical and between 10 mm and 15 mm in diameter.

11. The urethral compression device of claim 10 wherein the movement of the pawl past the teeth creates a clicking sound.

12. The urethral compression device of claim 9 wherein the "C" shaped element is biased towards an open position.

13. The urethral compression device of claim 9 where the "C" shaped element is with an inner circumference between 65 mm to 130 mm when the pawl is engaged between two adjacent ratcheting teeth in the teethed section of the ratcheting arm.

14. The urethral compression device of claim 9 wherein the compression element has a width of between 110 percent and 140 percent of the urethra.

15. The urethral compression device of claim 14 wherein the compression element has a width of approximately 130 percent of the urethra.

16. The urethral compression device of claim 9 wherein the C-shaped structure comprises a polymer material.

17. The urethral compression device of claim 16 further comprising a coating of polymeric material over a C-shaped metallic structure.

18. A urethral compression device comprising:
- a flexible member for enclosing a penis, the flexible member having a first end and a second end;
- a cylindrically shaped compression element carried by the member that compresses the urethra and having a width of between 100 percent and 150 percent of the penis, the compression element having a cavity and a distal surface extending about the cavity and connecting the first end and the second end; and
- a latching mechanism that retains the compression element in a radially inward position to compress the urethra of the penis.

* * * * *